United States Patent
Hansen

(10) Patent No.: US 7,192,549 B2
(45) Date of Patent: Mar. 20, 2007

(54) MOULDING METHOD, IN PARTICULAR A BLOWING OR VACUUM MOULDING METHOD FOR PRODUCTION OF A DISPENSING CONTAINER FILLED WITH A MEDIUM FOR DISPENSING

(76) Inventor: Bernd Hansen, Talstr. 22-30, Sulzbach-Laufen (DE) 74429

( * ) Notice: Subject to any disclaimer, the term of this patent is extended or adjusted under 35 U.S.C. 154(b) by 442 days.

(21) Appl. No.: 10/502,748

(22) PCT Filed: Jul. 10, 2003

(86) PCT No.: PCT/EP03/07452

§ 371 (c)(1),
(2), (4) Date: Jul. 28, 2004

(87) PCT Pub. No.: WO2004/033299

PCT Pub. Date: Apr. 22, 2004

(65) Prior Publication Data

US 2005/0156360 A1    Jul. 21, 2005

(30) Foreign Application Priority Data

Sep. 27, 2002   (DE) ............................... 102 45 318

(51) Int. Cl.
*B29C 39/02*   (2006.01)
(52) U.S. Cl. ...................................... 264/524; 264/525
(58) Field of Classification Search ................ 264/524, 264/525
See application file for complete search history.

(56) References Cited

U.S. PATENT DOCUMENTS

| 2,667,165 A | 1/1954 | Smith |
| 2,667,872 A | 2/1954 | Smith |
| 5,538,506 A | 7/1996 | Farris et al. |
| 5,687,550 A | 11/1997 | Hansen et al. |

FOREIGN PATENT DOCUMENTS

| DE | 44 39 231 C 1 | 4/1996 |
| DE | 197 07 292 A 1 | 8/1998 |

*Primary Examiner*—Suzanne E. McDowell
(74) *Attorney, Agent, or Firm*—Roylance, Abrams, Berdo & Goodman, L.L.P.

(57) ABSTRACT

The invention relates to a moulding method, in particular a blowing or vacuum moulding method for production of a dispensing container filled with a medium for dispensing. A moulding method for production of a dispensing container (1), filled with a medium for dispensing, comprises the following steps: introduction of an extruded plastic tube (6) into an open mould with moving main mould section (8) and mould section (10), cutting the plastic tube (6), spreading the plastic tube (6) into contact with the mould walls of the main mould section (8), filling the container (1) in the mould with the medium for dispensing, introduction of a sealing unit (3), closure of the mould section (10) and subsequent moulding of the section of plastic tube (6) running through the mould section (10) to give a protective sleeve (5) which encloses a cannula (11) in the sealing unit (3) as second component of the securing device (5, 17).

7 Claims, 8 Drawing Sheets

Figure 1:
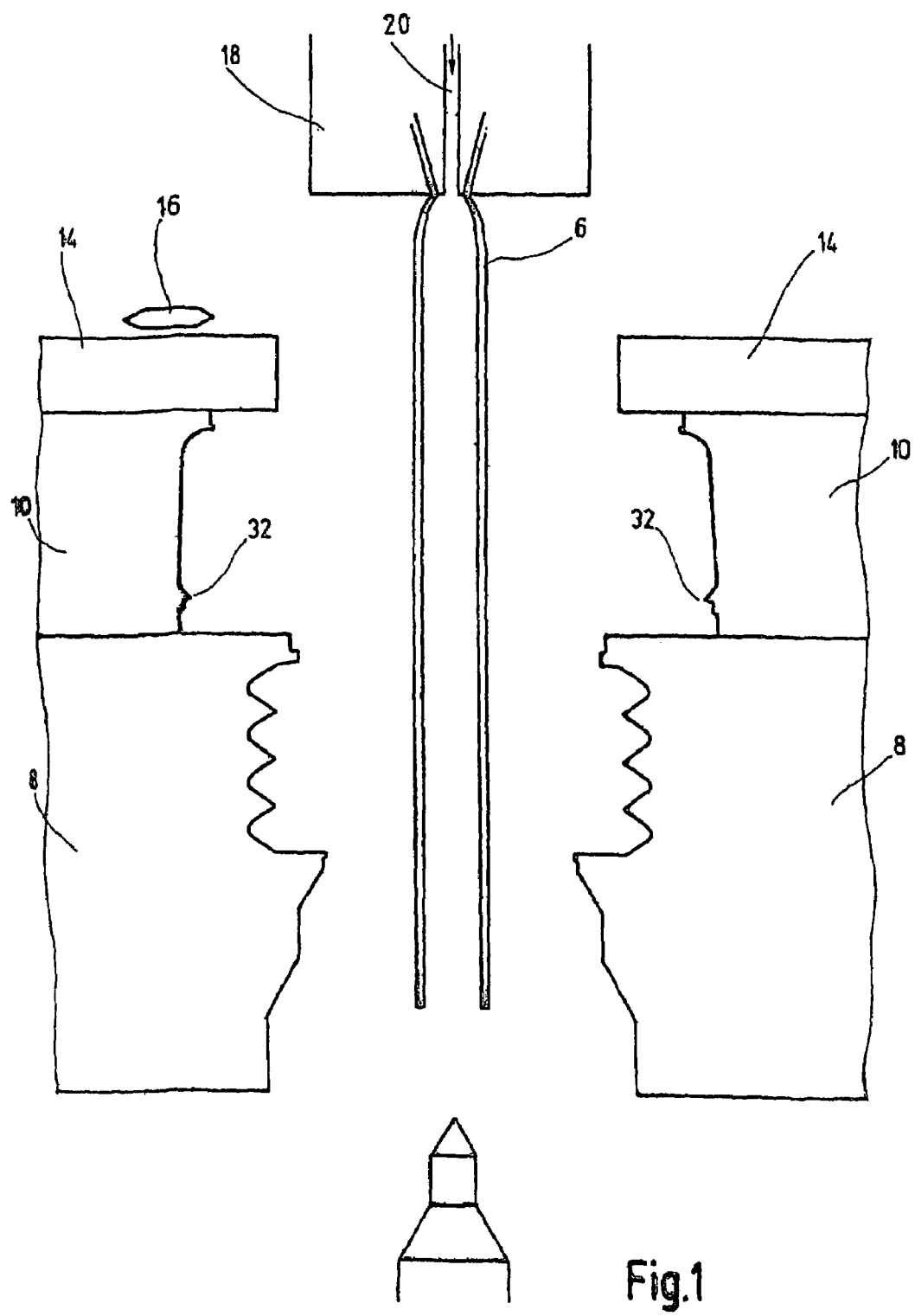

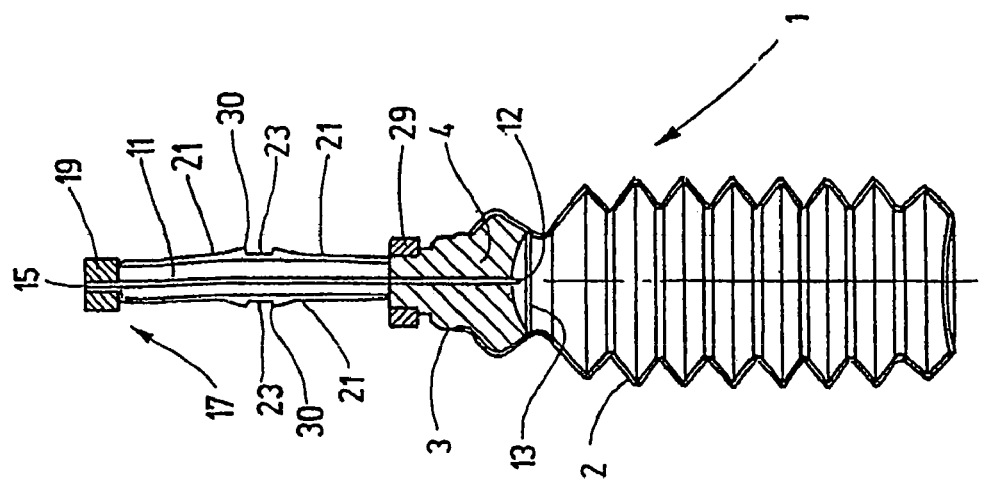
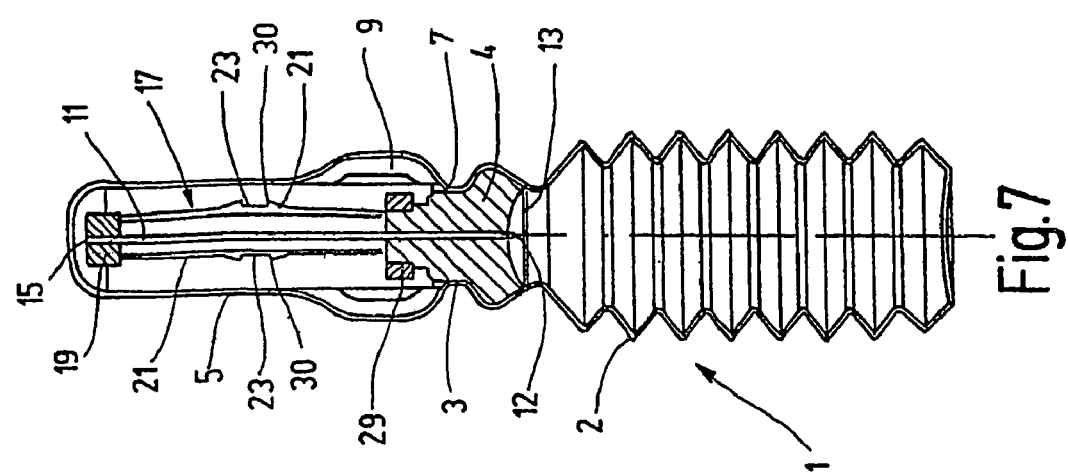
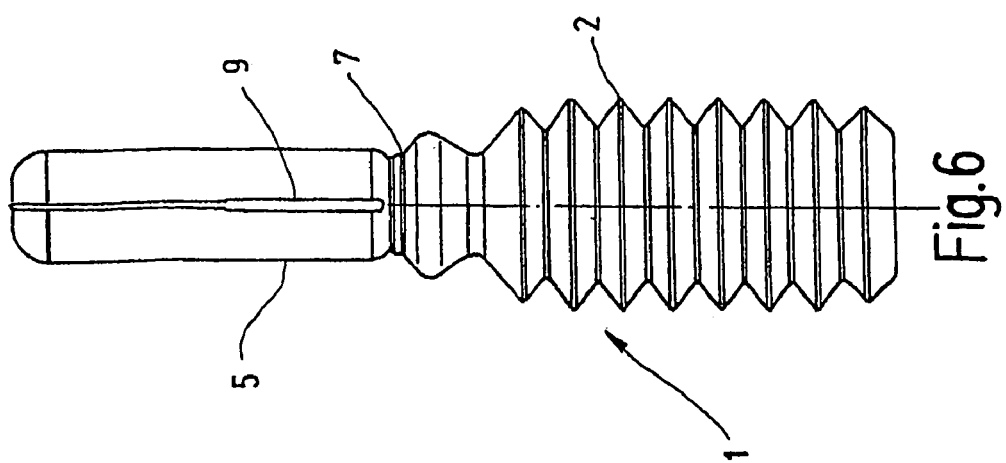

MOULDING METHOD, IN PARTICULAR A BLOWING OR VACUUM MOULDING METHOD FOR PRODUCTION OF A DISPENSING CONTAINER FILLED WITH A MEDIUM FOR DISPENSING

The invention relates to a moulding method, in particular a blowing and/or vacuum moulding method for production of a dispensing container filled with a medium for dispensing. The invention relates in particular to production of a dispensing container the primary but not exclusive purpose of use of which is represented by introduction of a desired volume of a medium, especially a liquid medium, into a receptacle. The medium to be introduced preferably is an additive, which, for example, is introduced as an additive admixture into a fluid present in the receptacle. The receptacle may be an infusion container with the contents of which the medium is to be mixed as an additive.

Use is customarily made for this purpose of a syringe the cannula (hollow needle) by means of which a perforable seal or plug of the receptacle, an infusion container, for example, is perforated, after which the medium is injected into the receptacle by expression of the syringe. This procedure requires the preliminary operational step of filling the syringe, the syringe being filled with the desired amount of the medium from a reservoir or the syringe being filled from a conventional vial holding the measured amount of the medium in question. One aspect of these decanting steps is that they are time-consuming, in that cannula and syringe must be removed from their packaging, the cannula mounted on the syringe, the vials opened or perforated, and the plunger of the syringe retracted. Another aspect is that a considerable risk of contamination of the medium exists when these measures are carried out.

Processes permitting simultaneous formation and charging of containers by blow molding or vacuum molding are already known. DE 197 07 292 A1, for example, discloses such a blow molding process. The invention has the object of disclosing, on the basis of such a blow molding process or a corresponding vacuum molding process, a production process for dispensing containers, one which both permits especially simple and efficient production of such dispensing containers and which is provided for production of dispensing containers which permit especially simple, rapid, and reliable dispensing of the medium from the dispensing container into a receiving container.

It is claimed for the invention that this object is attained by a molding process having the features specified in claim 1.

In that, as claimed for the invention, both formation of the container and its charging with a particular medium, as well as sealing of the charged container, including insertion of a sealing unit specifically designed for the dispensing process, with a safety device consisting of several components, take place inside a molding device, and consequently at the same place of production from which only the fully finished dispensing container need be transported, the result is especially simple production in which the sterility to be required may be guaranteed without difficulty.

In that, in the process claimed for the invention the dispensing container containing the medium combines the integrated cannula and a protective device covering one of the projecting ends of the needle, that is, the tip of the needle, to form one integrated unit, the desired quantity of the medium involved may be made ready in the dispensing container in advance of the dispensing process. Since the tip of the needle is covered by the protective device, the container with protected cannula may be handled directly in its state of readiness for the dispensing process. Intermediate steps of decanting of medium and preparation of a syringe are not required for the dispensing process. The desired simplification, saving of time, and increased safety from contamination are thus achieved. In the case of containers produced by the process claimed for the invention both the risk of contamination and the risk of harm to a user, such as a nurse, are greatly reduced, since the cannula is protected by the protective device again after use.

If the outer end of the cannula is provided for perforation of a perforable seal of a receiving container which is to receive the medium to be dispensed, the design of the protective device of the sealing unit may be such that, after removal of the protective hood, the element protecting the cannula may be returned to its operational position by resting against the seal when the seal is perforated by application of pressure to the protective element on the end of the cannula the latter may be returned to its operational position and to the protective position again after withdrawal of the cannula from the seal. Handling during the dispensing process is greatly simplified as a result.

In one especially advantageous exemplary embodiment of the molding process the steps of expansion and charging of the container present in the mold are carried out jointly by means of a combined blowing-charging mandrel extending through the insertion opening. This makes possible especially efficient production of charged containers with short cycle times.

In the course of molding of the protective hood as an integral part of the container and as a component of the protective device, a desired point of break is molded, preferably during closing of the mold section head jaw of the mold, in the area of transition between sealing unit and protective hood, on the wall of the latter. This point of break forms an area of separation which makes removal of the protective hood easier.

By preference at least one projecting grip end which forms a turning lever for easy manual separation of the protective hood is molded during closing of the mold section head jaws on the protective hood.

Figure 2:
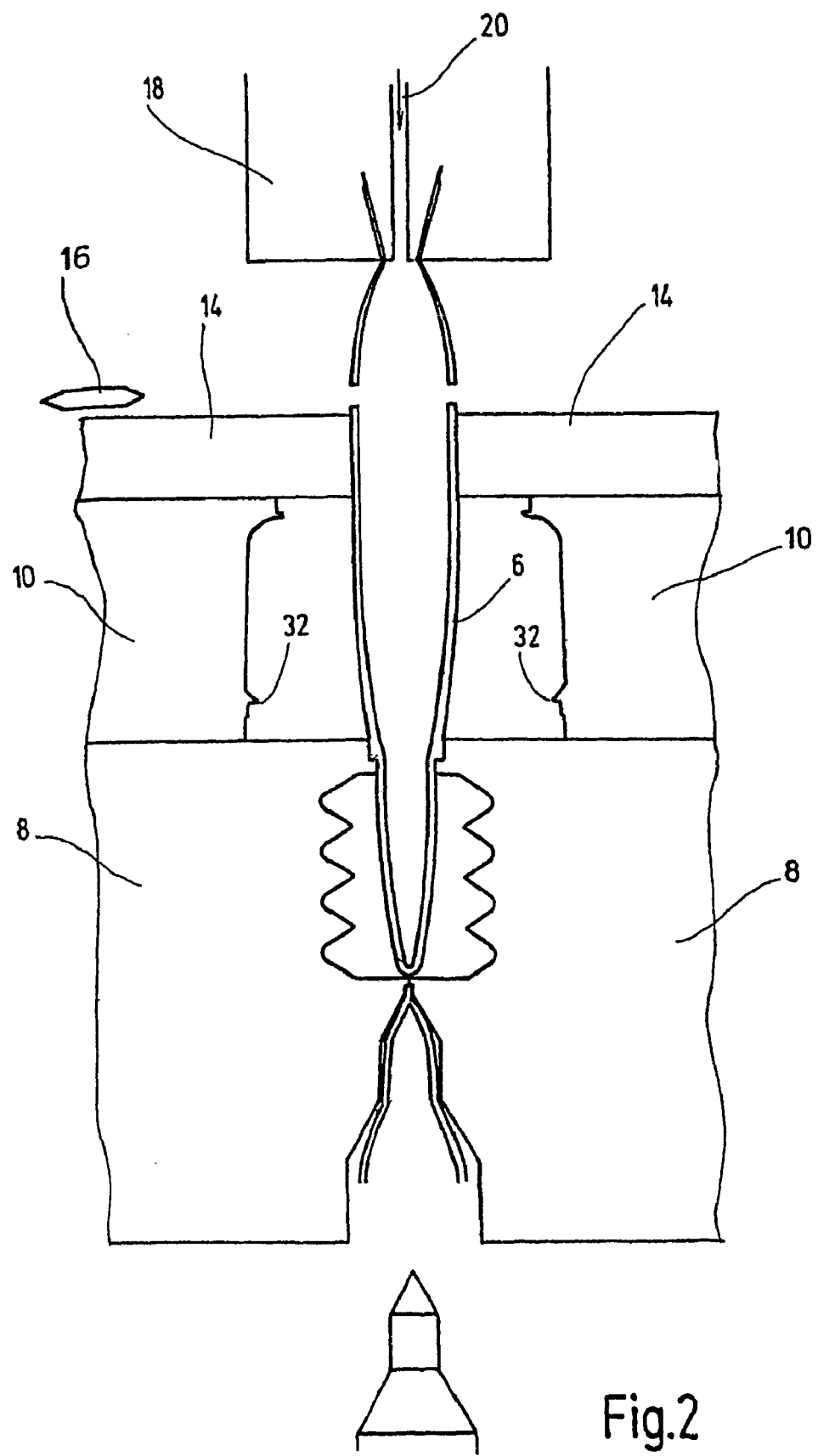
Figure 3:
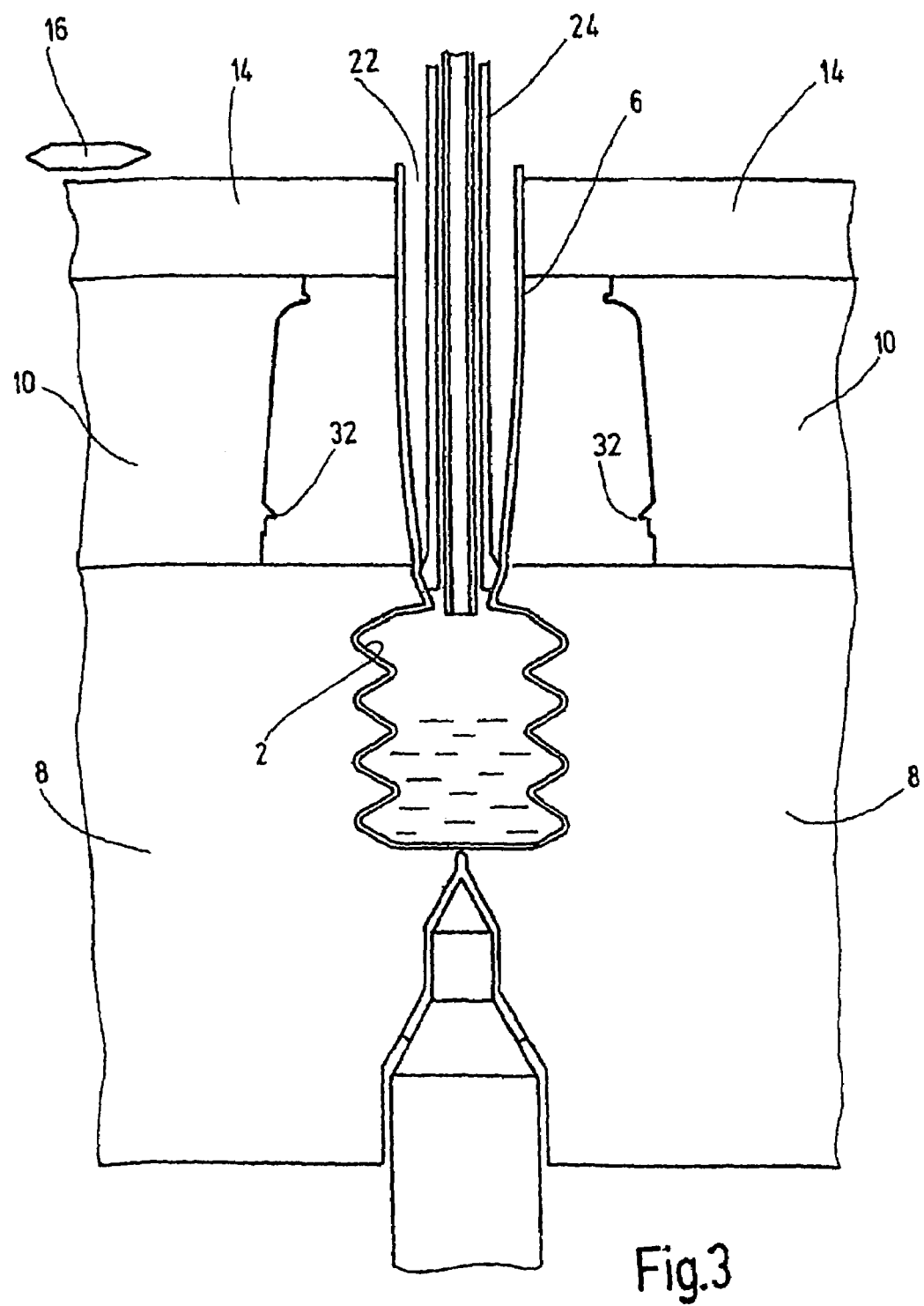
Figure 4:
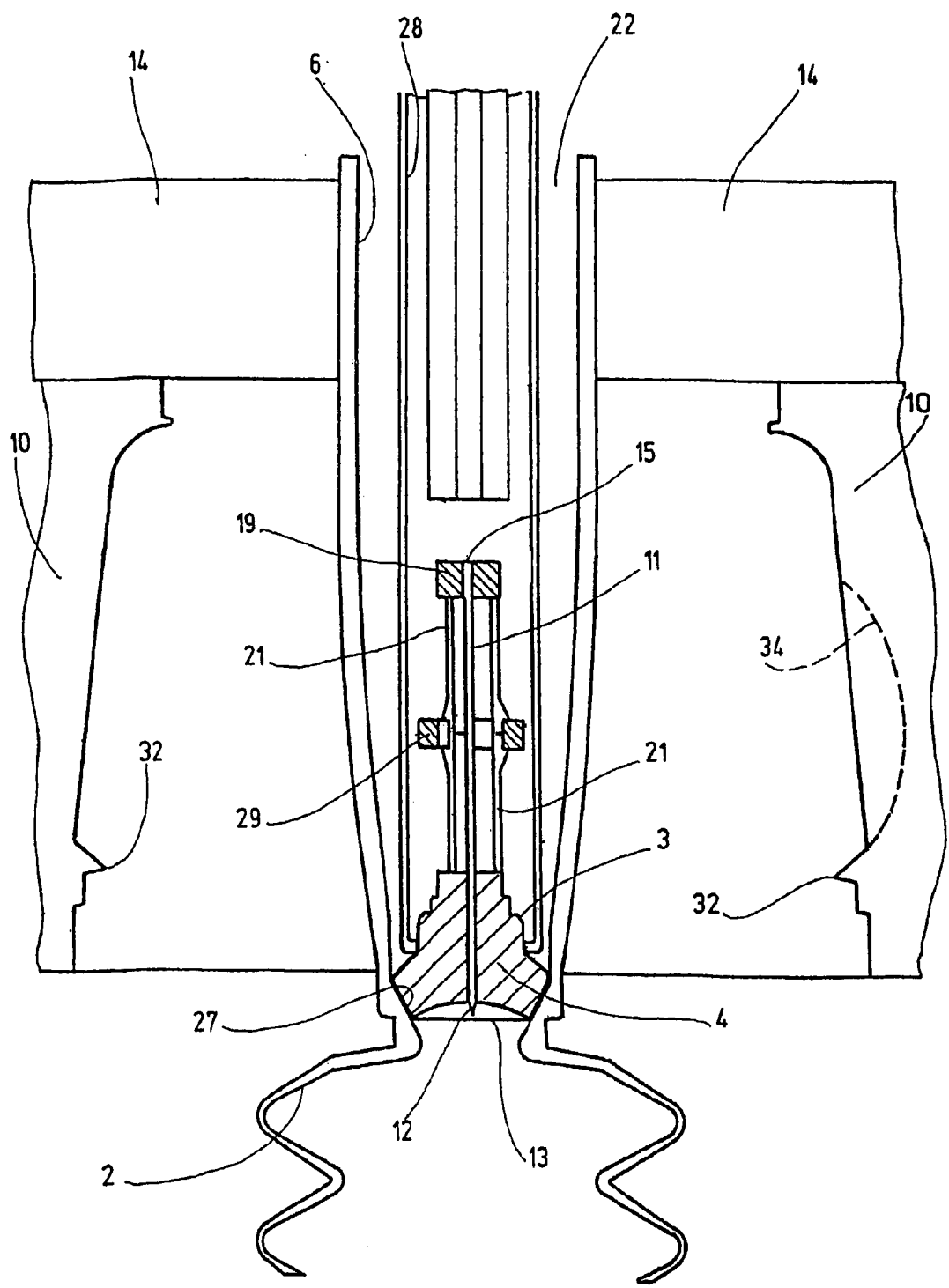
Figure 5:
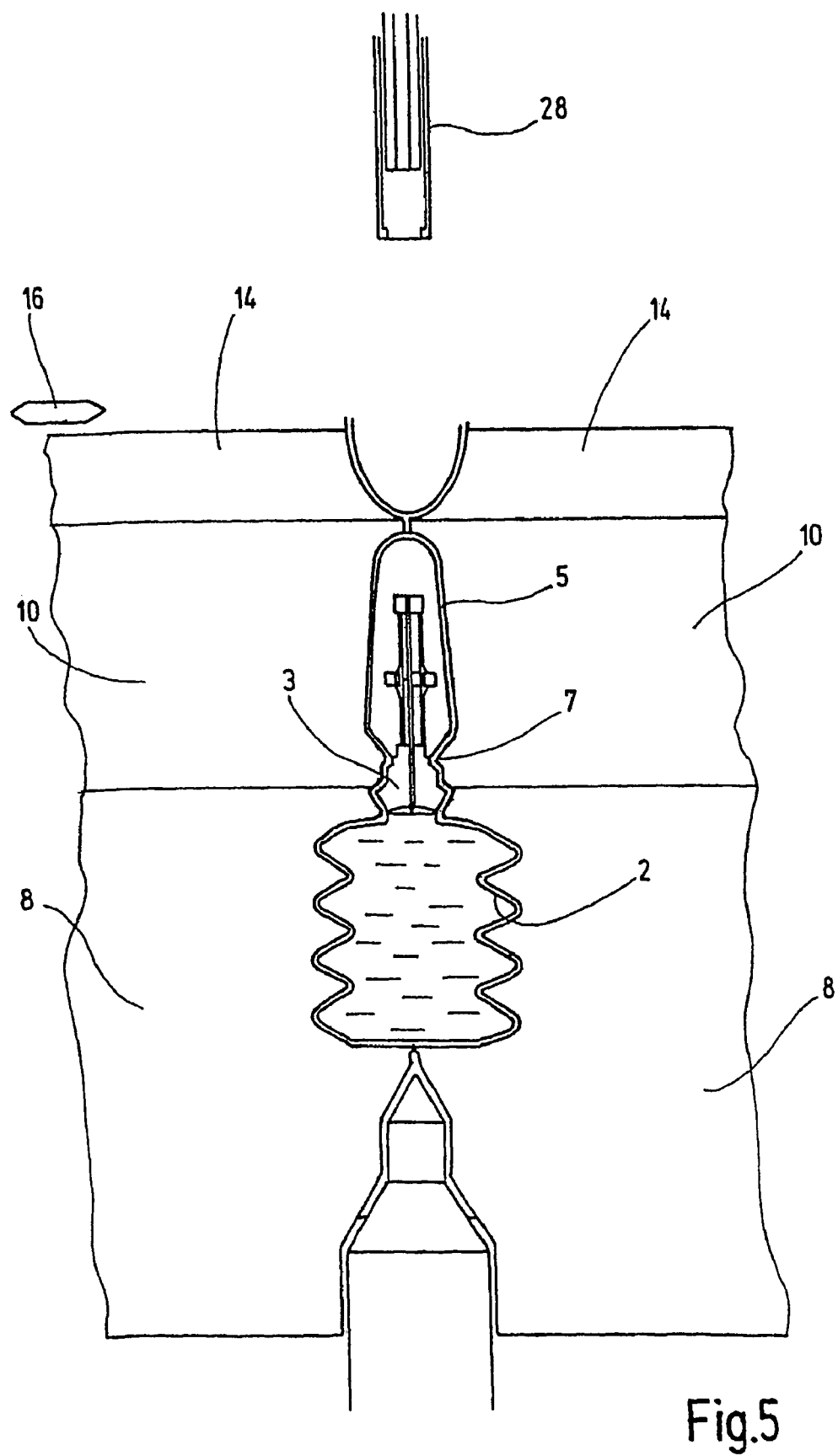
Figure 9:
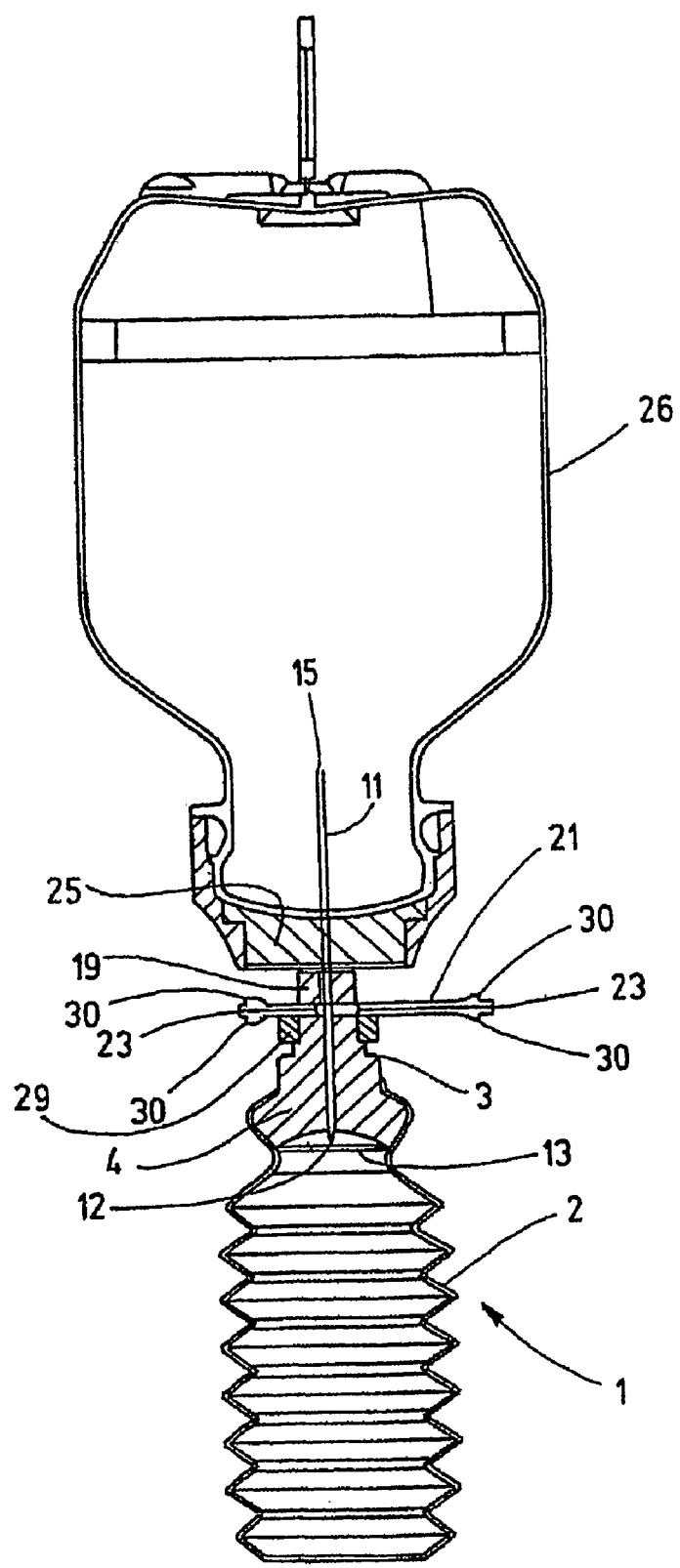
Figure 10:
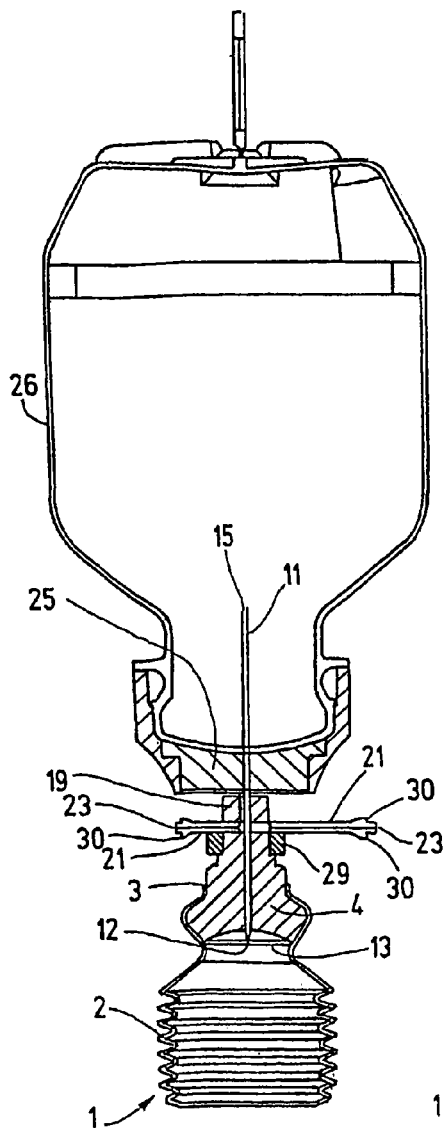
Figure 11:
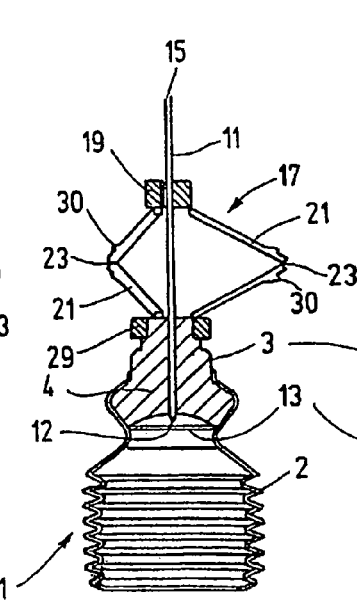
Figure 12:
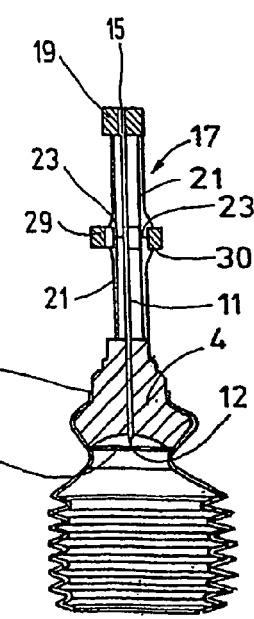

The invention is described in detail in what follows with reference to the drawing, in which FIGS. 1 to 3 present greatly simplified diagrams of essential elements of a molding device for application of the process claimed for the invention, several consecutive steps of the process being illustrated in these figures;

FIG. 4 presents an enlarged section illustrating the process step of introduction of a sealing unit associated with the container;

FIG. 5 a diagram on the scale of FIG. 1 to 3 showing the molding device, the step of molding a protective hood enclosing the sealing unit being illustrated;

FIG. 6 a side view of an exemplary embodiment of a dispensing container produced by the molding process claimed for the invention, in the operational situation preceding use, that is, with protective hood mounted;

FIG. 7 a longitudinal section of the dispensing container illustrated in FIG. 6;

FIG. 8 a longitudinal section corresponding to that in FIG. 7, but with the protective hood removed;

FIG. 9 a longitudinal section of the dispensing container in an operating state in which a dispensing cannula of the dispensing container has punctured a perforable sealing plug of an infusion container;

FIG. 10 an illustration similar to that of FIG. 9, but one in which the dispensing container has been expressed for dispensing of the medium contained;

FIG. 11 a longitudinal section of the dispensing container in the expressed state and after removal from the sealing plug; and FIG. 12 a longitudinal section of the dispensing container in an operating state corresponding to the protective position of one of the components of the protective device.

The figures present an exemplary embodiment of a dispensing container, designated as a whole as 1, produced by the process claimed for the invention. In the exemplary embodiment shown the dispensing container is a plastic container in the form of an ampule whose wall 2 is provided with folds and configured as a bellows, so that the dispensing container 1 in the configuration may be compressed from the configuration shown in FIGS. 6 to 9 (see FIGS. 10 to 12). A sealing unit 3 has been introduced into the dispensing container 1 in the neck area as an inserted component. As is to be seen the most clearly in FIGS. 4, 7, and 8, there extends through the central area of the sealing unit 3 a cannula 11 the inner end 12 of which extends slightly inward over the body 4 of the sealing unit 3. Between the inner end 12 of the cannula 11 and the interior of the dispensing container 1 there is a diaphragm 13 which is part of the inserted portion of the sealing unit 3. In addition, a first component 17 of a cannula protective device extending along the projecting part of the cannula is mounted on the body 4 of the sealing unit 3. A second component of this protective device is represented by a protective hood 5 enclosing the projecting part of the cannula 11 and forming an integral component of the container 1 during its production. The invention is explained in what follows with reference to the example of a blow molding process. Molding of the container with protective hood 5 could also be effected by a vacuum molding process or a combined blowing/vacuum molding process.

The operating sequence of the molding process is illustrated in FIGS. 1 to 5, in which the essential parts of a molding device are illustrated by greatly simplified diagrams. The device has three pairs of movable mold section jaws, specifically, primary mold section jaws 8 for molding the primary container component receiving a medium to be dispensed, mold section head jaws 10 for formation of the upper container component enclosing the sealing unit 3, in the present example the protective hood 5 of the protective device, and retaining jaws 14 for stabilization of an extruded plastic tube 6. The latter is extruded inward into the fully opened mold shown in FIG. 1 from a nozzle 18 which has a conventional connection 20 for delivery of support air, after which the primary mold section jaws 8 are closed and the retaining jaws 14 are moved onto the tube 6 and hold the tube 6 in a stable shape by means of a vacuum which is separated in the section between nozzle 18 and retaining jaws 14 by means of the knife 16. The stage of the process thereby reached is illustrated in FIG. 2, from which it may also be seen that the tube 6 is bonded by closing of the primary mold section jaws 8 on the leading end area for formation of the closed container bottom.

FIG. 3 shows that a movable combined blowing-filling mandrel 24 by which the tube 6 is expanded by means of blast air has been inserted through the insertion opening 22 which is formed by separation of the tube 6, so that the container wall 22 is adapted to the walls of the primary mold section jaws 8 in a bellows-like configuration, and also shows that, after the interior of the container has been shaped, the medium to be dispensed is introduced by means of the combined blowing-filling mandrel 24 (see FIG. 3).

In the immediately following process step the sealing unit 3 is inserted by means of a movable vacuum gripper 28 which may be introduced through the insertion opening 22 (see FIG. 4). As is to be seen from this figure, the body 4 of the sealing unit 3 has a tapered surface which rests against a seat 27 formed by the inner wall of the tube 6 in the area in which the mold walls of the primary mold section jaws 8 adjoin the mold section head jaws 10.

FIG. 5 shows that subsequently in the process the vacuum gripper 28 is moved away upward after the insertion process has been completed and the mold is now closed as a result of establishment of contact of the mold section head jaws 10 with each other, so that the section of the tube 6 extending in the area of the mold section head jaws 10 is molded to the protective hood 5.

As is to be seen the most clearly from the component diagram on an enlarged scale in FIG. 4, the mold section head jaws 10 have a mold projection 32 which forms on the tube 6, when the mold section head jaws 10 are closed, an annular notch which forms a desired point of break 7 at which the protective hood 5 may be conveniently separated from the rest of the container. As is to be seen from FIGS. 6 and 7, there is formed on the outside of the protective hood 5 a turning lever 9 formed as a handle permitting convenient manual rotation of the protective hood 5. The mold section head jaws 10 have, in diametrically opposite positions, recesses for the purpose of forming two opposite levers 9. Only one of these recesses 34 is indicated in FIG. 4, by a broken line.

Additional details of the cannula protective device, which, as has been pointed out, has the protective hood 5 as one component and has another component 17 illustrated in FIG. 4 and FIGS. 7 to 12, will now be discussed in detail with reference to FIGS. 7 to 12.

The cannula 11 extends from the outer end of the body 4 of the sealing unit 3 over a length which corresponds more or less to the length of a syringe cannula. FIGS. 6 and 7 illustrate operational situations in which the projecting outer end 15 of the cannula 11 is covered by the two components of the protective device and also by the protective hood 5 and by the component designated as a whole as 17.

This component 17 is integrally molded on the body 4 of the sealing unit 3 and has an annular element 19 which is movable on the cannula 11 and is in the protective position (see FIGS. 7, 8, and 12) on the outer end 15 of the cannula 11 so as to cover this end of the cannula, that is, the tip of the needle. The annular element 19 is integrally connected to the body 4 of the sealing unit 3 by way of rod-shaped bearing elements 21, the points of connection to annular element 19 and body 4 of the sealing unit 3 being in the form of flexible joints. In addition, at approximately one-half the length of the bearing elements 21 there are flectors 23 which divide the bearing elements 21. If the annular element 19 is displaced from the protective position to the service position of the dispensing container along the cannula 11 (see FIGS. 10 and 11), the sections of the bearing elements 21 adjoining the flectors 23 tilt so that they are forced apart from the cannula 11 and then move back together as shown in FIG. 10.

FIG. 10 and FIG. 9 referred to above show the container in the situation in which front end 15 of the cannula 11 has perforated a perforable seal 25 of an infusion container 26. The annular element 19 has been forced back from the protective position oriented toward the end 15 along the cannula 11 into the operating position. The pressure of the medium present in the dispensing container 1 is increased by compression of the bellows-like wall 2 of this container (see FIG. 10), so that the diaphragm 13 is pressed against the opposite end 12 of the cannula 11 and is perforated by the latter. Compression of the dispensing container 1 results in expression of the medium present in this container into the infusion container 26, so that an amount of an additive or agent corresponding the content of the dispensing container 1 is mixed with the content of the infusion container 26. For perforation of the diaphragm 13 the cannula 11 in the body 4 of the sealing unit 3 could also be guided for displacement limited by stops (not shown) in such a way that the cannula 11 is forced back on perforation of the seal 25 to the extent that its end 12 perforates the membrane 13.

FIG. 11 illustrates the operational situation after the expressed dispensing container 1 has been moved back again from the seal 25 of the infusion container 26. As a result of the inherent elasticity of the bearing elements 21, the annular element which previously had been forced back from the protective position during insertion of the cannula into the seal 25 as a result of application to the latter of the elasticity or retaining force of the bearing elements 21, is now automatically advanced by the force of elasticity to some extent against the end 15 of the cannula 11.

FIG. 12 illustrates the operational situation of the container after it has been used, the projecting outer end 15 of the cannula 11 being again secured by the component 17 of the protective device, even though the protective hood 5 is no longer in position. For this purpose a removable protective ring 29 seated on the body 4 of the sealing unit 3 is removed from the body 4 of the sealing unit and advanced along the cannula 11, it sliding over the bearing elements 21 and approaching the cannula from the position shown in FIG. 11, the annular element 19 being advanced to the end 15 of the cannula 11. The bearing elements 21 have stop notches 30 molded on the flectors 23, notches in which the protective ring 29 is caught (see FIG. 12).

After the protective ring 29 is caught in the stop notches 30 on the flectors 23 of the bearing elements 21, the cannula 11 is again covered by the annular element 19, which covers its end 15 despite removal of the protective hood 5, so that the container, now empty, may be safely disposed of. It is to be understood that the dispensing container may be used to advantage not only for admixing desired volumes of liquid media into infusion containers but equally for dispensing liquid, semisolid, or gaseous and/or particle-charged media, to the extent that dispensing by way of cannulas is possible or necessary.

The invention claimed is:

1. A moulding method, in particular a blowing and/or vacuum moulding method for production of a dispensing container (1) filled with a medium for dispensing, such method comprising the steps of introduction of an extruded plastic tube (6) into an opened mold having movable primary mold section jaws (8) and mold section head jaws (10), cutting the plastic tube (6) in the area situated outside the mold section head jaws (10) for formation of an insertion opening (22), closing the primary mold section jaws (8) for formation of the mold cavity for the dispensing container (1) and concomitant heat sealing of the plastic tube (6) in its fore area for formation of a container bottom, expansion of the plastic tube (6) for fitting on the mold walls of the primary mold section jaws (8) by blowing of air through the insertion opening (22) and/or by generation of a vacuum on the mold walls, charging of the container (1) present in the mold with the medium to be dispensed through the insertion opening (22), introduction of such sealing unit (3) through the section of the plastic tube (6) extending through the mould section head jaws (10) which has a dispensing cannula (11) projecting from its outer end for the medium, such cannula (11) having a securing device (5, 7) the first component (17) of which has a cannula protective element (19) which may be moved between an advanced protective position and a retracted service position, and closing of the mold section head jaws (10) and resulting molding of the section of the plastic tube (6) extending through the mold section head jaws (10) to form a protective hood (5) which encloses the cannula (11) of the sealing unit (3) as second component of the protective device (5, 17).

2. The molding process as claimed in claim 1, wherein the steps of expansion and charging of the container (1) present in the mold are carried out jointly by means of a combined blowing-filling mandrel (24) extending through the insertion opening (22).

3. The molding process as claimed in claim 1, wherein, when the mold section head jaws (10) of the mold is closed in the transitional area between sealing unit (3) and protective hood (5), a desired point of break (7) is formed on the wall of such protective hood (5).

4. The molding process as claimed in claim 3, wherein, when the mold section head jaws (10) on the protective hood (5) is closed, at least one projecting toggle (9) is formed as turning lever for separation of the protective hood (5) at the desired point of break (7).

5. The molding process as claimed in claim 3, wherein the sealing unit (3) with its sealing element (4) is introduced into a seat (27) formed by the mold wall sections of the closed primary mold section jaws (8) adjoining the mold section head jaws (10).

6. The molding process as claimed in claim 5, wherein a sealing unit (3) is introduced, the sealing element (4) of which extends through the seat (27) formed by the primary mold section jaws (8) jaws along the cannula (11) in the area of the mold section head jaws (10).

7. The molding process as claimed in claim 6, wherein the desired point of break (7) is formed at a distance from the seat (27) of the sealing element (4) in such a way that it encircles the sealing element (4) in the area into which mold section head jaws (10) extend.

* * * * *